(12) United States Patent
Morales et al.

(10) Patent No.: US 9,986,169 B2
(45) Date of Patent: May 29, 2018

(54) EXPOSURE CONTROL METHOD AND SYSTEM FOR AN IMAGE CAPTURE DEVICE

(71) Applicant: KARL STORZ, Imaging, Inc., Goleta, CA (US)

(72) Inventors: Efrain O. Morales, Santa Barbara, CA (US); Jonathan Bormet, Goleta, CA (US)

(73) Assignee: KARL STORZ, Imaging, Inc., Goleta, CA (US)

(*) Notice: Subject to any disclaimer, the term of this patent is extended or adjusted under 35 U.S.C. 154(b) by 359 days.

(21) Appl. No.: 15/015,836

(22) Filed: Feb. 4, 2016

(65) Prior Publication Data
US 2017/0230558 A1     Aug. 10, 2017

(51) Int. Cl.
| H04N 5/00 | (2011.01) |
| H04N 5/235 | (2006.01) |
| H04N 5/232 | (2006.01) |
| H04N 5/225 | (2006.01) |
| H04N 5/357 | (2011.01) |
| G06K 9/46 | (2006.01) |

(52) U.S. Cl.
CPC .............. *H04N 5/235* (2013.01); *G06K 9/46* (2013.01); *H04N 5/2256* (2013.01); *H04N 5/23238* (2013.01); *H04N 5/357* (2013.01); *G06K 2009/4666* (2013.01)

(58) Field of Classification Search
CPC ........................... H04N 5/235; H04N 5/23238
USPC .......................................................... 348/36
See application file for complete search history.

(56) References Cited

U.S. PATENT DOCUMENTS

| 5,713,053 | A | 1/1998 | Hirai | |
| 7,538,801 | B2 | 5/2009 | Hu | |
| 8,814,782 | B2 | 8/2014 | Hale | |
| 2005/0212955 | A1* | 9/2005 | Craig | H04N 5/232 |
| | | | | 348/362 |
| 2014/0036050 | A1 | 2/2014 | Yoshino | |
| 2014/0081083 | A1 | 3/2014 | Morita | |
| 2014/0092226 | A1 | 4/2014 | Kuriyama | |
| 2014/0247376 | A1 | 9/2014 | Kuwata | |
| 2014/0307111 | A1 | 10/2014 | Nishigori | |
| 2015/0237262 | A1 | 8/2015 | Hamada | |

OTHER PUBLICATIONS

Hongqin, Li, Real-Time Digital Image Exposure Status Detection and Circuit Implementation, (IJACSA) International Journal of Advanced Computer Science and Applications, vol. 6, No. 5, May 3, 2015, China.

* cited by examiner

*Primary Examiner* — Jeffery Williams
(74) *Attorney, Agent, or Firm* — Michael Joseph Loi; David Noel Villalpando

(57) ABSTRACT

Improved exposure control processes, devices, and systems are provided for wide angle lens imaging systems that suffer from image distortion. The exposure control uses a model of the wide angle lens distortion that estimates the weights that respective pixels of the image would have when producing an undistorted version of the image signal, and then scales pixel intensity values by the respective weights to produce weighted pixel values. The weighted pixel values are provided to an exposure control pixel counting process to produce one or more exposure feedback control signals, which control exposure features of the imaging system.

20 Claims, 11 Drawing Sheets

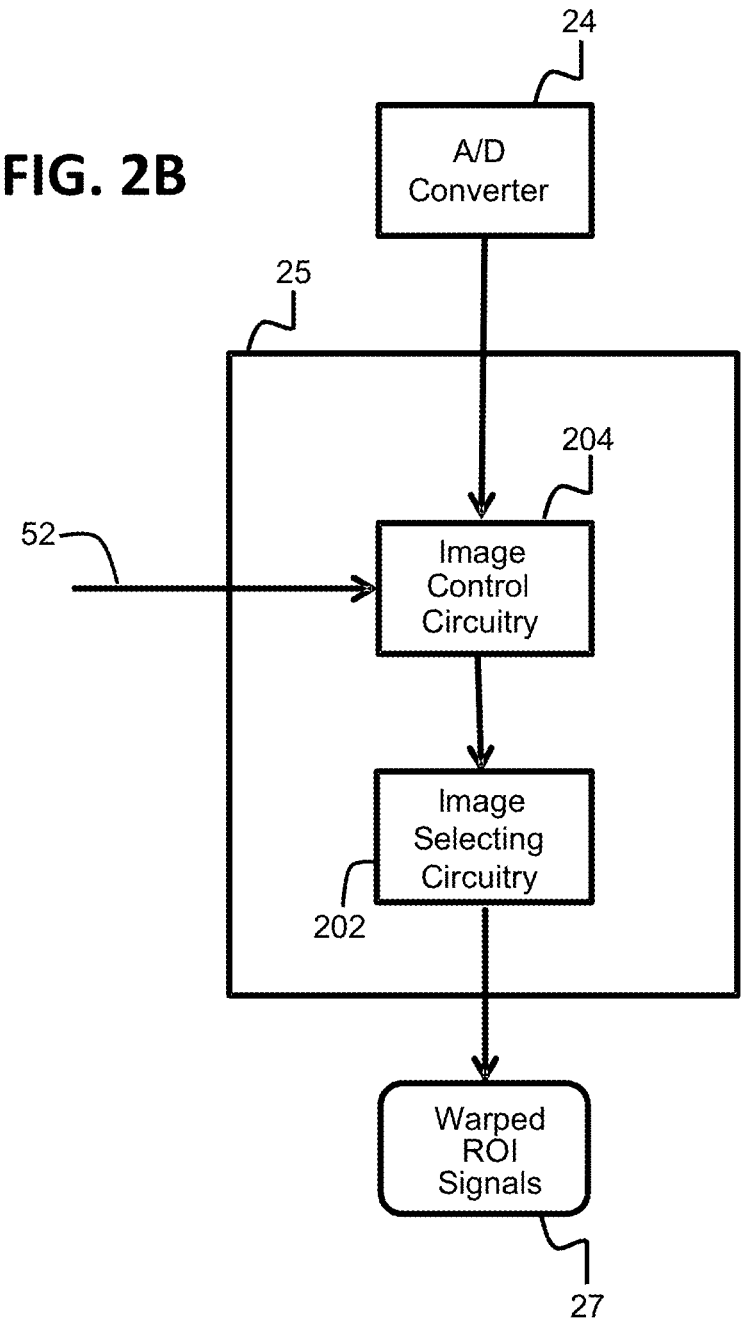

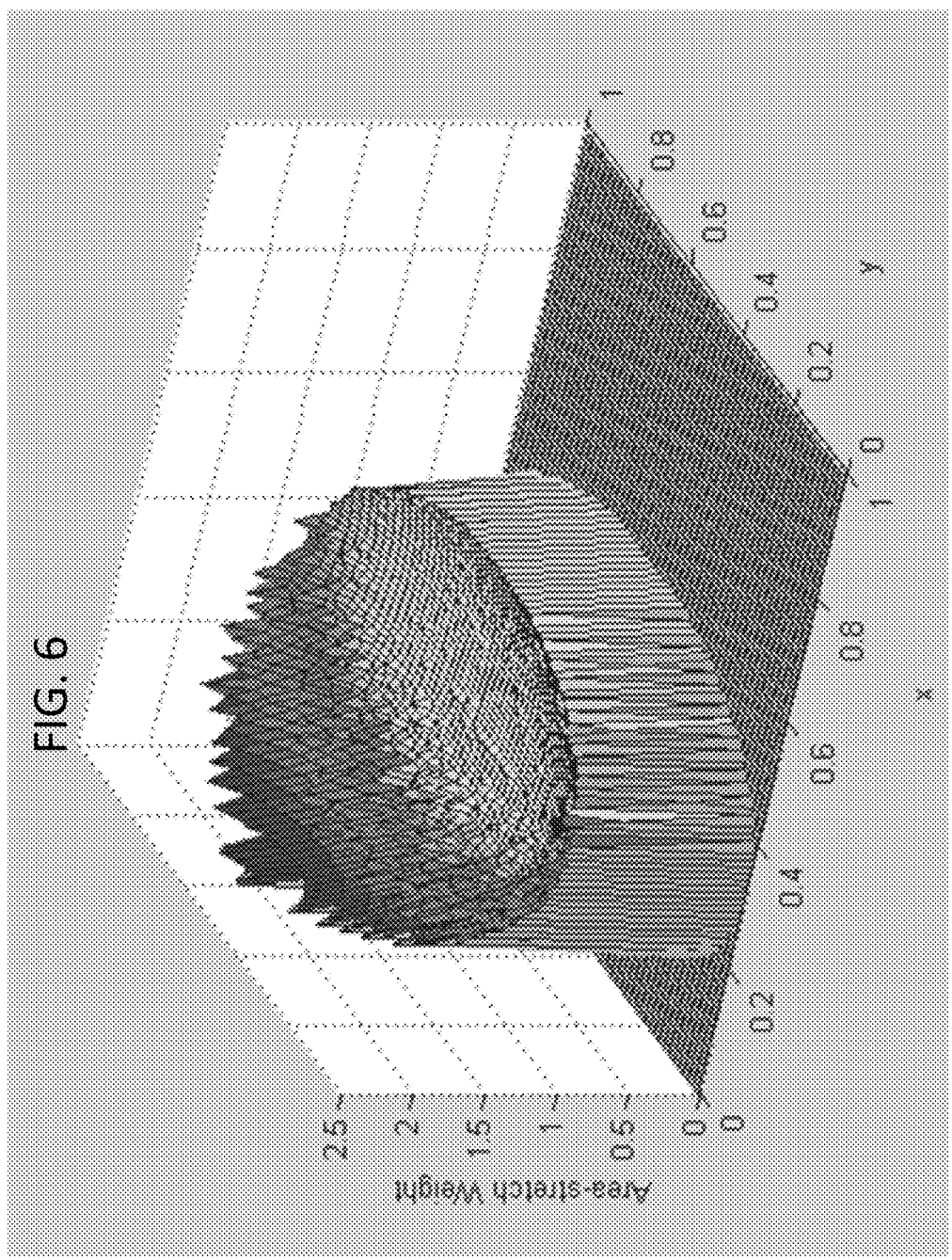

EXPOSURE CONTROL METHOD AND SYSTEM FOR AN IMAGE CAPTURE DEVICE

TECHNICAL FIELD OF THE INVENTION

The invention relates generally to the field of image capture and more specifically to exposure control in an imaging system that captures a distorted image with an image capture device having a wide-angle lens that distorts (warps) the field of view, and undistorts the distorted image with image processing.

BACKGROUND OF THE INVENTION

The solid-state look-around (SSLA) endoscope incorporates very wide-angle optics which capture a large field of view. A SSLA endoscope typically has an actual angle of view which is non-zero (meaning the scope lens is tilted relative to the axis of the scope rod). During a procedure, a doctor will select a different display angle of view from a range of programmed possibilities. An unwarping and rotation algorithm may then simulate an image as if the actual viewing angle were the same as the selected display angle of view. In such simulation, a large portion of the captured image (also called the sensor image) is not used, but rather only the pixels inside a region of interest (ROI) are used to form the displayed image. The captured image typically includes warping or distortion due to the use of a wide angle lens. Such distortion may include highly non-linear barrel distortion in which the image magnification increases non-linearly with the distance from the axis of the optical system. The distortion typically needs to be corrected to view useful images from the endoscope. The correction requires processing the image using knowledge of the distortion resulting from the wide angle lens and other optical elements, typically with a relatively slow image processing technique that non-linearly resamples the image to produce the unwarped displayed image data.

To obtain quality images using endoscopes, exoscopes, borescopes, or other imaging devices, the image exposure must be controlled. This involves adjusting elements such as the light source, light source intensity, the optical assembly aperture, and the shutter speed or time for which image sensor integrates charge for each image frame. Most prior art methods for exposure control include steps wherein the number of image pixels that have a digital value above or below predetermined thresholds are counted. If the number is too high, the exposure is controlled downward (faster exposure) to avoid overexposure, and if the number is too low, the exposure in controlled upward to avoid underexposure. When device produces distorted images, it is the undistorted version that should best be used to produce accurate counts of the number of pixels above or below the thresholds, because the undistorted image is the image that is viewed, analyzed, and stored. However, prior-art imaging systems typically count pixels of the distorted image, and therefore do not provide accurate pixel counts of the corresponding undistorted image. It is possible to count the pixels in the undistorted image, but this causes delays in the result and can thus delay the automatic exposure control loop. U.S. Publication No. 20140092226 by Kuriyama describes an automatic exposure control device that adjusts exposure values linearly based on a pixels distance from the center of an automatic exposure area. U.S. Publication No. 20140081083 by Morita et al. describes an exposure control process that can calculate exposure to control brightness corresponding to a particular area of a scope's image.

What is needed are improved ways to control exposure in devices having wide angle lenses.

SUMMARY OF THE INVENTION

It is an object of the invention to provide improved control of the exposure of images from endoscopes or other imaging devices (e.g., exoscopes, borescopes), through counting pixels in a distorted image that are above or below a threshold for exposure control such that the effects of the unwarping are included in the exposure control. This has the advantage of improving image quality over prior systems that control exposure with the distorted or warped image data. It is another object of the invention to provide faster feedback control of imaging devices to enable real time feedback control of video signals, and to provide efficient distortion models for achieving the same for one or multiple regions of interest viewable by a device. This has the advantage of showing smooth, clear video and improving various feedback control issues that result slow exposure control.

According to a first aspect of the invention, an exposure control process is used that, within a selected region of interest, applies a predetermined weight to each pixel location of the distorted image. The predetermined weight for a pixel location may depend on the number of times the pixel value at that location is used to produce a pixel in the undistorted image. The weight for a pixel location also may depend on the weighting applied to each instance a pixel is used to produce a pixel in the undistorted image. The weights are used to scale the pixel intensity values (e.g., pixel luminance values, pixel color values, and/or other lightness intensity controlling values) for all pixel locations of interest, which are then summed to produce a pixel count that is representative estimate of the pixel counts as if they had been counted in the unwarped image. In some versions, the region of interest and viewing angle may be changed by a selection corresponding to a sub-set of pixels available from the image sensor.

According to a second aspect of the invention, a solid-state look-around endoscope is provided that includes an improved exposure control system employing the first aspect of the invention. The viewing angle of the device may be changed by selection of a sub-set of pixels of the image sensor that corresponds to the desired region of interest. Further, the invention's techniques can be generally applied to an automatic exposure control technique for warped images (e.g., images captured with a fish-eye lens) produced from other devices.

In a third aspect, an imaging scope system is provided including a light emitting element, an optical assembly including a wide angle lens element, and an image sensor assembly including an image sensor configured to receive at least a portion of light focused through the optical assembly and produce output signals. Image forming circuitry receives the output signal and produces an image signal, but the image signal includes distortion resulting from the wide angle lens element. Exposure control circuitry is coupled to receive the image signal from the image forming circuitry, and coupled to the light emitting element, the image sensor, and the optical assembly to perform feedback control. The exposure control circuitry models an inverse effect of the distortion by (i) estimating pixel weights that respective pixels of the image signal including distortion have when producing an undistorted version of the image signal and (ii)

scaling pixel intensity values by respective pixel weights to produce a weighted value for the pixels. The weighted pixel values are provided to an exposure control pixel counting process to produce one or more exposure feedback control signals. These are transmitted to the device's light emitting element, the optical assembly, or the image sensor assembly. The system also has image processing circuitry configured to receive the image signal including distortion and produce an undistorted version of the image signal.

In some implementations of any of the above aspects of the invention, the exposure control circuitry is configured to operate in parallel to the image processing circuitry. The exposure control circuitry may be configured to provide the weighted pixel values to the exposure control pixel counting process as part of a digital signal processing sequence before the image processing circuitry produces the undistorted version of the image signal. In some versions, the exposure feedback control signals take effect on the imaging device for the subsequent image frame from which the exposure levels are calculated. The image forming circuitry may include image selecting circuitry that receives the image signal and produces a region of interest signal that corresponds to a region of interest that is less than the entire image area carried in the image signal. In some versions, the region of interest and viewing angle may be changed by a selection corresponding to a sub-set of pixels available from the image sensor. The exposure control circuitry may be formed in a field programmable gate array (FPGA) or a graphics processing unit (GPU), or may be split between or among processing devices.

When estimating pixel weights, the circuitry may evaluate first coefficients which describe curves from which the pixel weight estimates are calculated using the respective pixel's coordinates. These first coefficients may include cubic spline coefficients or quadratic polynomial coefficients. The use of such coefficients allows the storage of an accurate pixel weight model with little memory compared to storing the pixel weights themselves. The first coefficients may be produced by evaluating second coefficients of second curves which describe the values of the first coefficients as a function of a viewing angle of the device.

According to a forth aspect of the invention, a method is provided to control the image exposure on an imaging device. The method includes receiving a series of sequential image frames including multiple pixels from an imaging device having a wide angle lens that produces distortion. The method activates a first distortion model for estimating a pixel weight that the distorted image pixels would have in an undistorted version of an image frame. To control exposure of the imaging device, the method uses the required pixels, and scales each pixel intensity value by a respective pixel weight from the first distortion model to produce a weighted pixel value for each pixel. These values are fed to an exposure control pixel counting process to produce one or more exposure level signals. From these signals, the method creates exposure feedback control signals that are transmitted to the relevant parts of the imaging device in such a manner that they control exposure features of the imaging device. The feedback signals may control the integration time on an imaging array sensor of the imaging device, or the brightness of a light source of the imaging device, the aperture of the imaging device, or other exposure related functions. In some versions, the exposure feedback control signals take effect on the imaging device for the subsequent image frame from which the exposure levels are calculated.

The method also produces an undistorted version of the image frame, preferably independently of the exposure control steps.

In some implementations of the forth aspect, in response to instructions, the method adjusts the image devices angle of operation and activates a second distortion model for performing exposure control at the new angle of operation, and starts working with a stream of image frames produced at the new angle. In some versions, the region of interest and viewing angle may be changed by a selection corresponding to a sub-set of pixels available from the image sensor. A device may store a distortion model for each angle of view which the device may be configured to observe. The distortion models may be stored more efficiently by storing coefficients of curves that describe the models.

The process of activating a distortion model may include evaluating first coefficients which describe curves from which the weight of a respective pixel is calculated using the respective pixel's coordinates. The first coefficients may include cubic spline coefficients and quadratic polynomial coefficients. The first coefficients may be produced by evaluating second coefficients of second curves which describe the values of the first coefficients as a function of a viewing angle of the device.

In some implementations of the forth aspect, the imaging device is a medical scope (e.g., an endoscope or exoscope) configured to allow a user to select from multiple regions of interest viewing at multiple respective angles of view, with the method further including storing a respective distortion model for each of the regions of interest. Other versions may work with other types of imaging devices.

Implementations of the invention may also be embodied as software or firmware, stored in a suitable medium, and executable to perform various versions of the methods herein. These and other features of the invention will be apparent from the following description of the preferred embodiments, considered along with the accompanying drawings.

BRIEF DESCRIPTION OF THE DRAWINGS

FIG. 2B is a block diagram showing more detail ROI production circuit of FIG. 2A.

FIG. 6 shows an example area-stretch weight surface plotted over an image device area.

DETAILED DESCRIPTION OF EXAMPLE EMBODIMENTS

The invention provides improved control of exposure for imaging devices with a wide angle lens system, such as an endoscope device that gathers an endoscopic image field at least spanning the longitudinal axis relatively large angles off of the longitudinal axis. A preferred version is employed in an endoscope such as the one described in U.S. Pat. No. 8,814,782 to Hale, et al, issued Aug. 26, 2014, which is hereby incorporated by reference. The techniques and features herein may also be embodied in other types of image capture devices, digital microscopes, certain digital cameras, virtual reality (VR) cameras and VR camera rigs of multiple cameras, mobile phones equipped with imaging sub-systems, and automotive vehicles equipped with imaging sub-systems, for example.

Figure 1A:
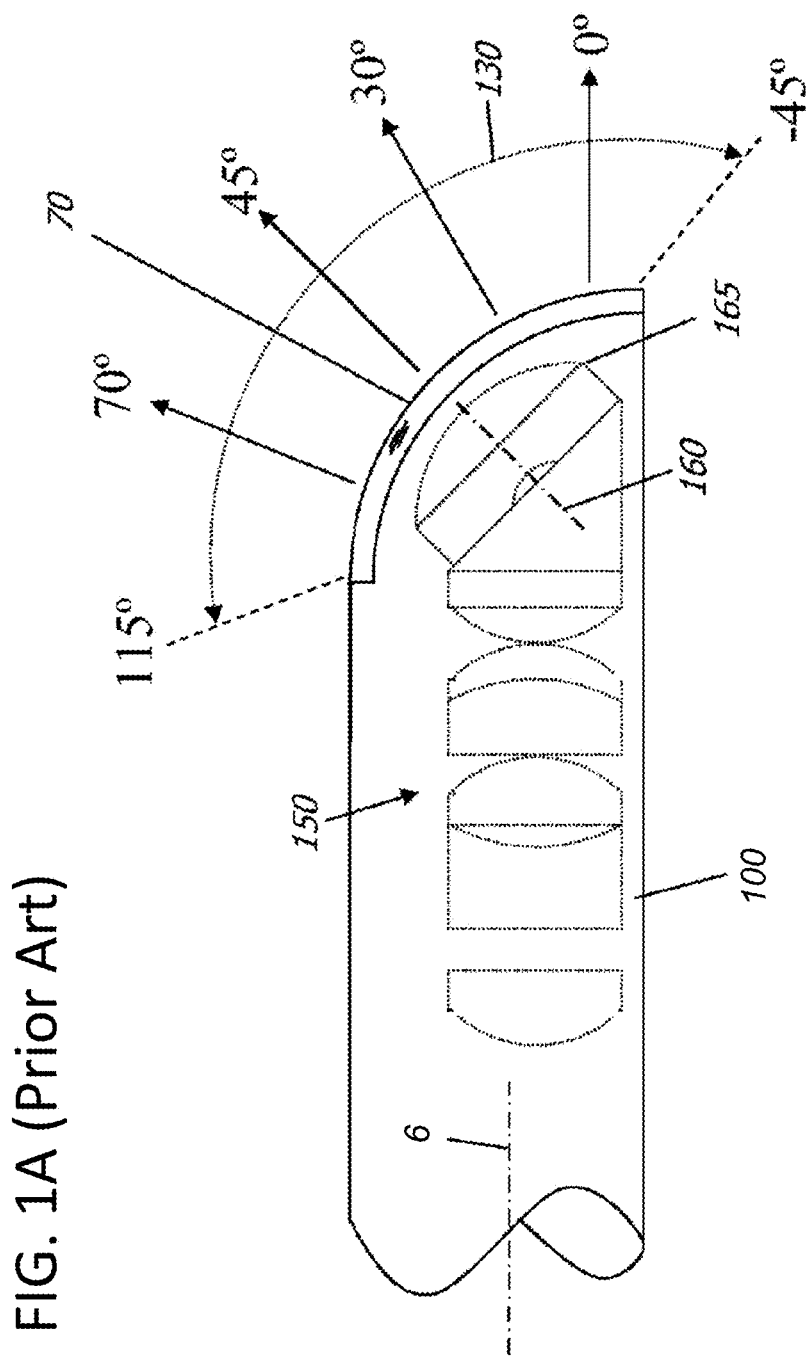
FIG. 1A is cross-section of the distal end of a prior art wide-angle endoscope in which the invention may be implemented.
Figure 1B:
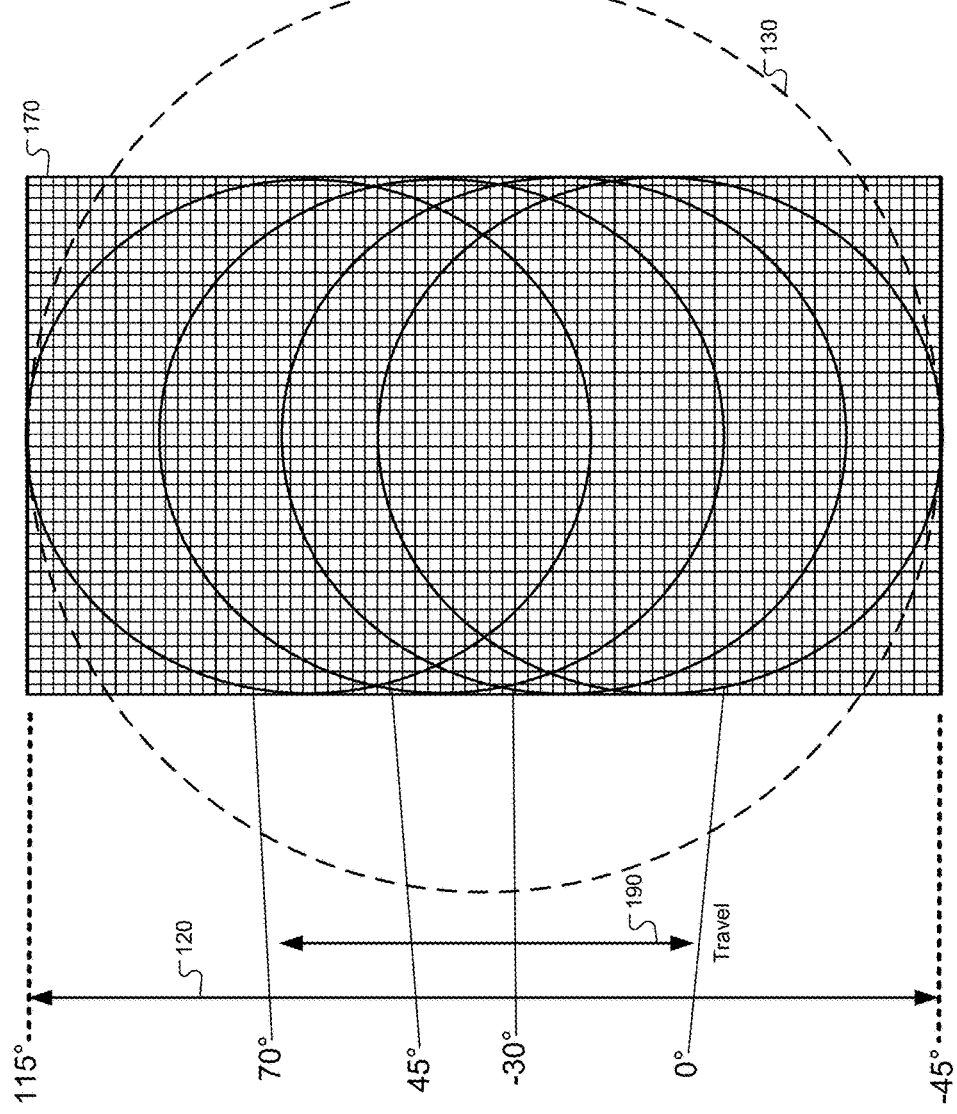
FIG. 1B is a depiction of the image sensor of the same prior art endoscope relative to the endoscopic field of view.

FIG. 1A shows a cross section of a distal tip 100 of a prior art wide-angle endoscope in which the invention may be implemented. The depicted distal tip 100 has longitudinal axis 6, a viewing window 70, and an optical assembly including a wide angle lens system 165 with optical center 160 and a transmission system 150. FIG. 1B is a diagram depicting an image sensor of the same prior art endoscope relative to the endoscopic field of view. As shown in FIG. 1B, in some versions, the region of interest and viewing angle may be changed by a selection corresponding to a sub-set of pixels available from the image sensor. The same scheme may be employed in other devices that are not endoscopes. Referring to both Figures, the optical center 160 is angularly offset from the longitudinal axis 6 of the endoscope 100 and covers a viewing range 120 of 160 degrees from −45 to +115 degrees relative to the longitudinal axis. From this configuration, the wide angle lens system 165 simultaneously gathers an endoscopic image field 130 that spans the longitudinal axis and an angle greater than ninety degrees to the longitudinal axis. As a result, the simultaneous image field gathered by the endoscope provides both forward and retrograde imaging. Providing a variable view endoscope that spans this range is beneficial because it enables a user to view objects that reside in front of the endoscope and behind the standard fields of view for endoscopes. This improves the ability of a user to safely operate and handle the device in the body cavity. Further by incorporating a wide angle lens with an optical center that is angularly offset relative to the longitudinal axis, the endoscope can more accurately mimic the viewing capabilities and function of a fixed angle endoscope.

The image field gathered by wide angle lens system 165 is conveyed to transmission system 150, which in turn conveys the wide angle field of view to an image sensor surface area 170 that comprises image surface area 170 formed by a plurality of pixels that gather light images and convert the images to output signals. The image surface area 170 is preferably rectangularly shaped with a longitudinal dimension that is greater than its lateral dimension, but can also be a variety of different shapes, such as square, circular or oval. Also, it is preferable that the image surface area 170 has an HD aspect ratio of 16:9. Since a wide-angle lens system can provide uneven information distribution, without correction an HD image sensor enables the crowded information regions to be captured and displayed on a monitor. As shown in FIG. 1B, image surface area 170 partially captures field 130. It is preferable that the longitudinal dimension of image surface area 170 substantially correspond to the entire longitudinal dimension of field 130. This enables the endoscopic system to provide the user with an image or a range of regions of interest that span the field of view of the endoscope. However, image surface area 170 only captures a portion of the lateral dimension of field 130. The lateral dimension of area 170 can be chosen such that the distortion of an image laterally is minimal and not detected by the human eye. Further, by limiting the lateral dimension of the sensor, the cross-sectional area of the endoscope can be more efficiently used. For instance, the lateral dimension of the wide angle lens can be reduced and consequently reduce the overall size of the endoscope. Also, the area of the field of view not captured by the sensor can be used carry a fiber optic illumination system.

FIG. 1B also depicts specific regions of interest (ROIs) at 0, 30, 45 and 70 degrees which can be selected by a user over a designated range 190. A region of interest is an image area formed on the image surface area that is a subset of the overall field of view captured by the sensor. The center of the area of the ROI corresponds to a selected viewing angle chosen by a user, in this case a longitudinal viewing angle, but other offset directions may be used. The overall area of the ROI can correspond to the field of view typically provided by a fixed angled endoscope for that same angle. Alternatively, the overall area of the ROI can be chosen to provide a minimal distortion variation across the overall area. Still further, the overall area of the ROI can be chosen such that the field encompassed by a viewing angle at least partially overlaps with an adjacent standard viewing angle, such as 30 and 45 degrees. ROIs that are sized to overlap with adjacent viewing angles assist a user in maintaining orientation in the event that a viewing angle is changed.

Because digital cameras and scopes employing imaging devices and related circuitry for signal capture, processing, correction, and exposure control are well-known, the present description will be directed in particular to elements forming part of, or cooperating more directly with, methods, and apparatus and program products in accordance with example embodiments of the invention. Elements not specifically shown or described herein are selected from those known in the art.

Figure 2A:
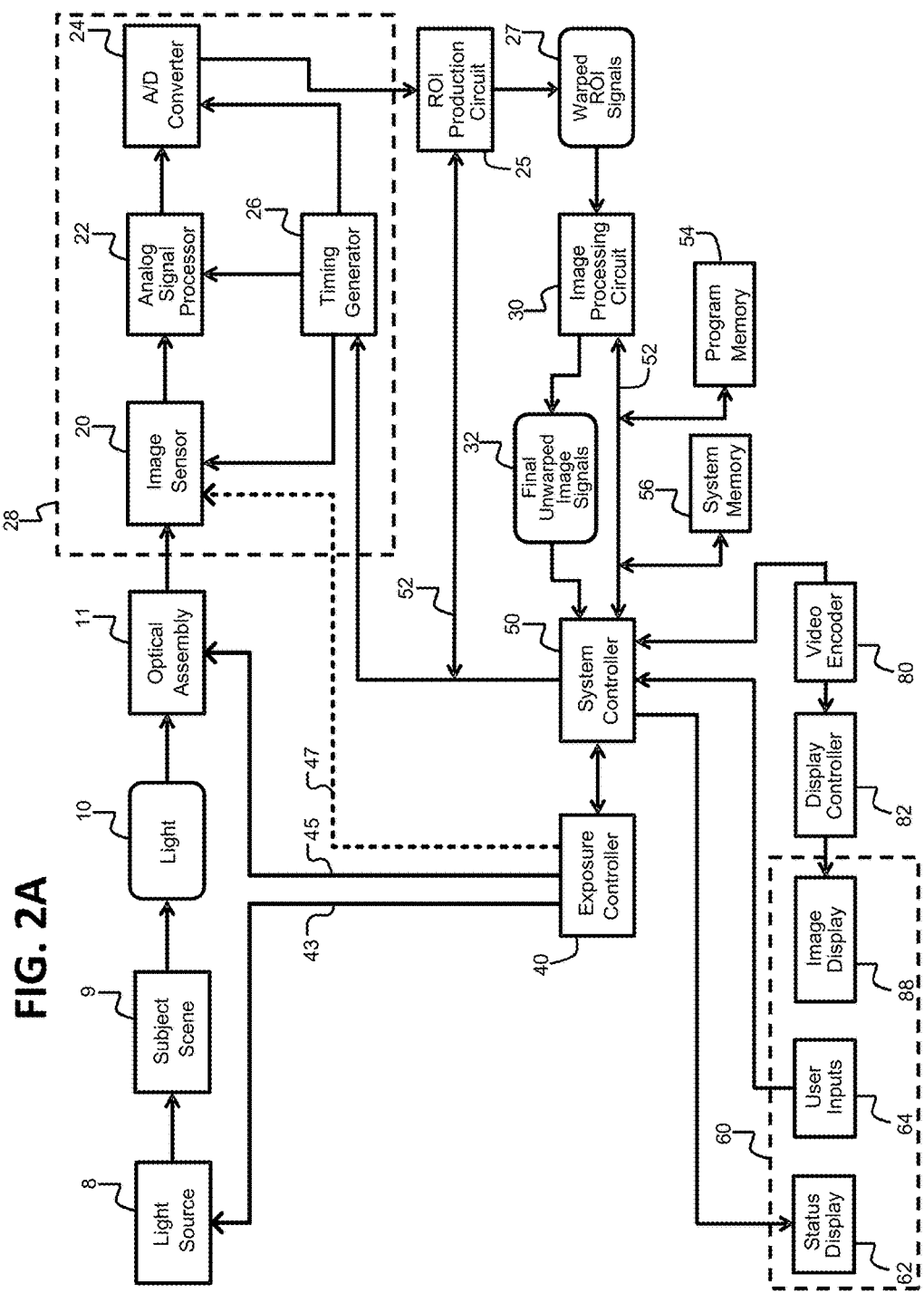
FIG. 2A is a hardware block diagram of an example image capture device according to an example embodiment of the invention.

FIG. 2A is a hardware block diagram of an example image capture device according to an example embodiment of the invention. While a diagram is shown for a medical scope and its associated display system, the invention is applicable to more than one type of device enabled for image capture, such as endoscopes incorporating solid state imagers, digital microscopes, digital cameras, VR camera rigs, mobile phones equipped with imaging sub-systems, and automotive vehicles equipped with imaging sub-systems, for example. A light source 8 illuminates subject scene 9 and light 10 reflected from (or, alternatively, transmitted by or through) the subject scene is input to an optical assembly 11, where the light is focused to form an image on solid-state image sensor 20. The light source may take any suitable form of light emitting element, including a fiber optic light transmission assembly to which an internal or external light source may be connected. Optical assembly 11 includes at least one wide-angle lens element, and preferably a wide angle lens system such as system 165 of FIG. 1, such that optical assembly 11 focuses light which represents a wide field of view. Image sensor 20 converts the incident light to an electrical signal by integrating charge for each picture element (pixel). The image sensor 20 of the preferred embodiment is an active pixel complementary metal oxide semiconductor sensor (CMOS APS) or a charge-coupled device (CCD). The total amount of light 10 reaching the image sensor 20 is regulated by the light source 8 intensity, the optical assembly 11 aperture, and the time for which the image sensor 20 integrates charge. An exposure controller 40 responds to the amount of light available in the scene given the intensity and spatial distribution of digitized signals corresponding to the intensity and spatial distribution of the image focused on image sensor 20. To perform fast and accurate control, exposure controller 40 uses exposure level signal 302 (FIG. 2C) calculated from the warped or distorted ROI pixel data 27 received at signal processor 30, as further described below.

In use, an analog signal from the image sensor 20 is processed by analog signal processor 22 and applied to analog-to-digital (A/D) converter 24 for digitizing the analog sensor signals. ROI (region of interest) production circuit 25 produces warped ROI signals 27 by identifying and selecting, as directed by system controller 50, a region of interest within the captured image. The warped ROI signals 27 describe a series of images frames that are warped, i.e. spatially distorted, as an effect of the optical assembly 11 using a wide-angle lens. The resulting warped ROI signals 27 are transmitted to the image processing circuit 30. It is noted that while this embodiment of the invention employs a ROI selection from a larger array of available image data, other versions may use the entire field of data received from image sensor 20. Timing generator 26 produces various clocking signals to select rows and pixels and synchronizes the operation of image sensor 20, analog signal processor 22, and A/D converter 24. Image sensor stage 28 includes the image sensor 20, the analog signal processor 22, the A/D converter 24, and the timing generator 26. The functional elements of the image sensor stage 28 can be fabricated as a single integrated circuit as is commonly done with CMOS image sensors or they can be separately-fabricated integrated circuits.

Image processing circuit 30 is one of three programmable logic devices, processors, or controllers in this embodiment, in addition to a system controller 50 and the exposure controller 40. Although this distribution of imaging device functional control among multiple programmable logic devices, programmable logic devices, and controllers is typical, these programmable logic devices, processors, or controllers can be combinable in various ways without affecting the functional operation of the imaging device and the application of the invention. These programmable logic devices, processors, or controllers can comprise one or more programmable logic devices, digital signal processor devices, microcontrollers, or other digital logic circuits. Although a combination of such programmable logic devices, processors, or controllers has been described, it should be apparent that one programmable logic device, digital signal processor, microcontroller, or other digital logic circuit can be designated to perform all of the needed functions. All of these variations can perform the same function and fall within the scope of this invention.

In the illustrated embodiment, image processing circuit 30 manipulates the digital image data according to processes that are either programmed into the circuit (in the case of programmable logic devices) or loaded into the circuit program memory as programming instructions (in the case of processors and controllers such as a graphics processing unit (GPU)). The digital image data manipulation includes, but is not limited to, image processing steps such as color filter array demosaicing, noise reduction, color correction, and gamma correction. In this version the digital image data manipulation performed by image processing circuit 30 also includes and calculating the exposure level signals 302 (FIG. 2C) and unwarping the image data within the selected ROI to produce final unwarped image signals 32.

The system controller 50 controls the overall operation of the image capture device based on a software program stored in program memory 54. This memory can also be used to store user setting selections and other data to be preserved when the camera is turned off. System controller 50 controls the sequence of image capture by directing exposure controller 40 to set the light source 8 intensity, the optical assembly 11 aperture, and the time for which image sensor 20 integrates charge (integration time), directing the timing generator 26 to operate the image sensor 20 and associated elements, and directing image processing circuit 30 to process the captured image data. A data bus 52 includes a pathway for address, data, and control signals, and connects system controller 50 to image processing circuit 30, program memory 54, system memory 56, timing generator 26 and other related devices. Exposure controller 40 may also be connected to data bus 52, or may have a separate bus or signal lines connecting to system controller 50. Exposure controller 40 is configured to control exposure features of the imaging device using one or more exposure feedback control signals. In this version, three exposure feedback control signals are shown, a light source control signal 43, an aperture control signal 45, and an integration time control signal 47 (which is shown in dotted lines because it is typically not a direct signal path, but is implemented through system controller 50 indirectly to control image sensor 20 such as by controlling the timing generator 26). These signals respectively allow the exposure controller to set the exposure light source 8 intensity, the optical assembly 11 aperture, and the time for which the image sensor 20 integrates charge. While three exposure feedback control signals are shown in this embodiment, other versions may use any one or two of these, or may include additional signals to control exposure characteristics of the device, such as a gain value amplifying one or more signal values from the image array, for example.

After the image processing is complete, the processed image data is continuously sent to video encoder 80 to produce a video signal. This signal is processed by display controller 82 and presented on image display 88. This display is typically a liquid crystal display backlit with light-emitting diodes (LED LCD), although other types of displays are used as well. The processed image data can also be stored in system memory 56 or other internal or external memory device.

The user interface 60, including all or any combination of image display 88, user inputs 64, and status display 62, is controlled by a combination of software programs executed on system controller 50. User inputs typically include some combination of typing keyboards, computer pointing devices, buttons, rocker switches, joysticks, rotary dials, or touch screens. The system controller 50 manages the graphical user interface (GUI) presented on one or more of the displays (e.g. on image display 88). The GUI typically includes menus for making various option selections.

FIG. 2B shows in more detail the ROI production circuit 25 from FIG. 2A. When a user selects a region of interest viewing angle through user inputs 64 of user interface 60, the system controller 50 transmits via data bus 52 a region of interest field selection that is received by image control circuitry 204. Image control circuitry 204 in turn produces a field control signal used to identify a portion of the captured image, the ROI, associated with the user selection. Image selecting circuitry receives the field control signal to identify and select the portion of the captured image to produce warped ROI signals 27 containing the image data for the series of warped image frames in accordance to the region of interest viewing angle selected by the user. In some versions the ROI is a square or rectangular region and the signals produced from ROI production circuit 25 contain images with the desired ROI boundaries, while in other versions the ROI may be circular (a traditional view used in medical scope devices, for example), and warped ROI signals 27 may contain rectangular warped images that require further masking of areas to produce a final unwarped image signals 32.

Figure 2C:
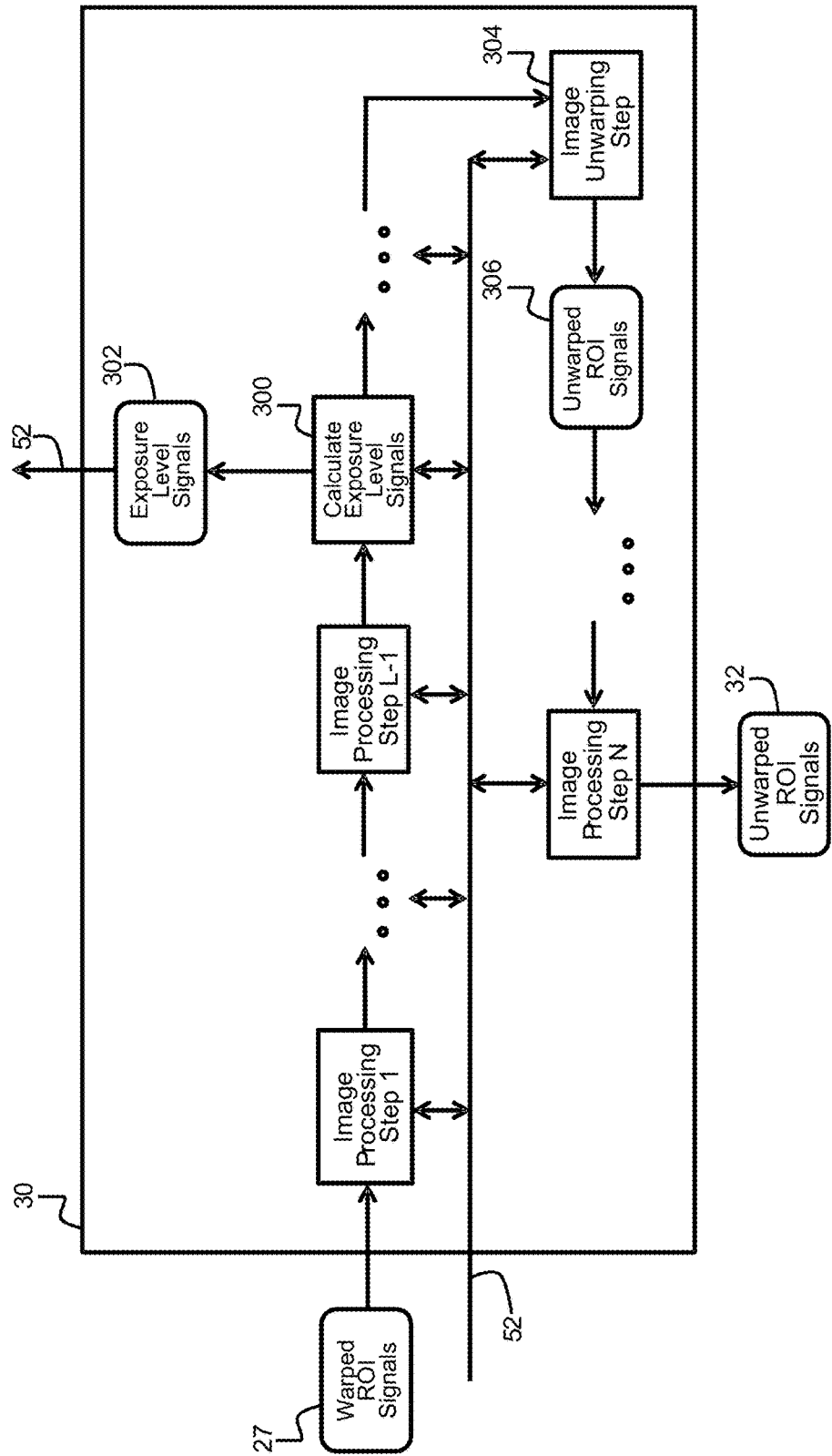
FIG. 2C is a functional block diagram showing more detail of an example processing circuit of FIG. 2A.

FIG. 2C shows in more detail the example image processing circuit 30 from FIG. 2A, which processes the image data of each frame to produce the desired form of image from the data received. Image processing circuit 30 generally performs several image processing steps, reflected in the depicted sequence of in which there are N number of image processing steps. Zero or more image processing steps precede the calculate exposure level signals step 300, which is the Lth step and produces exposure level signals 302. Zero or more steps may follow the calculate exposure control signals step 300 before performing the image unwarping step 304, which produces unwarped image signals 306. Zero or more steps follow the image unwarping step 304 to produce the final unwarped image signals 32. Data bus 52 transports the exposure level signals 302 to the system controller, or directly to the exposure controller 40, and transfers other information both ways between the system controller 50 and each of the image processing steps. The transported information typically includes image processing step parameters and user-selected option indicators.

While FIG. 2C shows versions of the invention in which the imaging processing steps are all performed consecutively (i.e. in series) following a single data path, other variations are possible wherein at least two of the image processing steps are performed in parallel following two or more data paths and that perform the same function as described and shown in FIG. 2C. It is noted that the step of producing unwarped ROI signals 306 does not require output from the step of calculating exposure level signals 300, and so these processes may be performed in parallel by different processing cores, different threads, or different processors or digital logic, and the result of the exposure level signal calculation 300 be passed to exposure controller 40. The exposure level signal calculation 300 is preferably conducted independently of the unwarped ROI signal calculation 306, and block 300 may be conducted before or in parallel with block 306. All of those variations fall within the scope of the invention.

The depicted loop of calculating exposure level signals 302 from the warped image data in signals 27, and using the exposure level signals to generate exposure control feedback signals 43, 45, and 47, represents a real-time control loop that automatically adjusts the exposure level no matter what viewing angle of the device. In one embodiment, the real-time control loop accepts a distortion variable or area stretch weight for each pixel that reflects a weighted contribution of captured-imaged pixels within a region of interest (ROI) of the warped image. The pixels are weighted according to how much the pixel is "stretched" when later providing an undistorted image to display, save, and/or analyze. The area stretch weights are preferably generated with a distortion model, as further described below, but may be stored directly or otherwise calculated based on known distortion characteristics of the device's optical assembly.

The depicted real-time exposure control loop requires quick, but accurate processing. The most intensive part of the processing to produce the exposure level signals is pixel counting, wherein pixels with a digital value above or below a threshold are counted. For warped images, the relative contribution of the pixel, as projected on an un-warped or undistorted image, should be accounted for since the capture imaged undergoes unwarping/stretching algorithms prior to display or storage. Pixel counting can be done on a processed (un warped) image, but unwarping typically takes too long for real-time needs. The techniques herein incorporate the unwarping effects in the pixel counting process. For example, a predetermined area-stretch weight of pixel location may depend on the number of times the pixel value at a location is used to produce a pixel in the stretched/undistorted image. The area-stretch weight may be based on an optic model that accounts for FOV (field of view), actual viewing angle, and distortion characteristic function of the wide angle lens and the remaining optical assembly (the other lenses and optical elements through which the image light passes before hitting the sensor). The area-stretch weights can either be stored in memory blocks or calculated by a subsystem, which uses knowledge of the unwarping algorithm as further described below. Because the pixel-counting is done within an automatic real-time exposure control loop, the counting must be done quickly enough such that there is no substantial delay in producing a real-time control signal. Real-time in this context typically means that the counting is done quickly enough to keep up with the frame rate of the system, so that the exposure control feedback controls signals may be generated based on each image. Depending on the timing of the image sensor, this may allow the exposure control feedback signals to be received and the new settings take effect before the next frame of data is acquired from the imaging sensor (a blanking interval often leaves time between frames of acquired data). In such cases, real-time feedback control provides that the effects of the feedback are seen on the very next frame. In some cases, the feedback control signals will take effect two frames after the frame from which the exposure level signals are calculated. Real-time may also mean that the pixel counting and exposure feedback control signal generation is done before the current image frame has finished its image processing, the remaining processing steps in FIG. 2C, for example. Since unwarping algorithms are relatively slow, it is difficult to first unwarp the distorted image and then do the pixel-counting to produce the control signal in the time allotted. It is therefore advantageous to count pixels of the distorted image in a way that the counting includes the effects of the unwarping, such as with the area-stretch weights used in the preferred version herein.

Figure 2D:
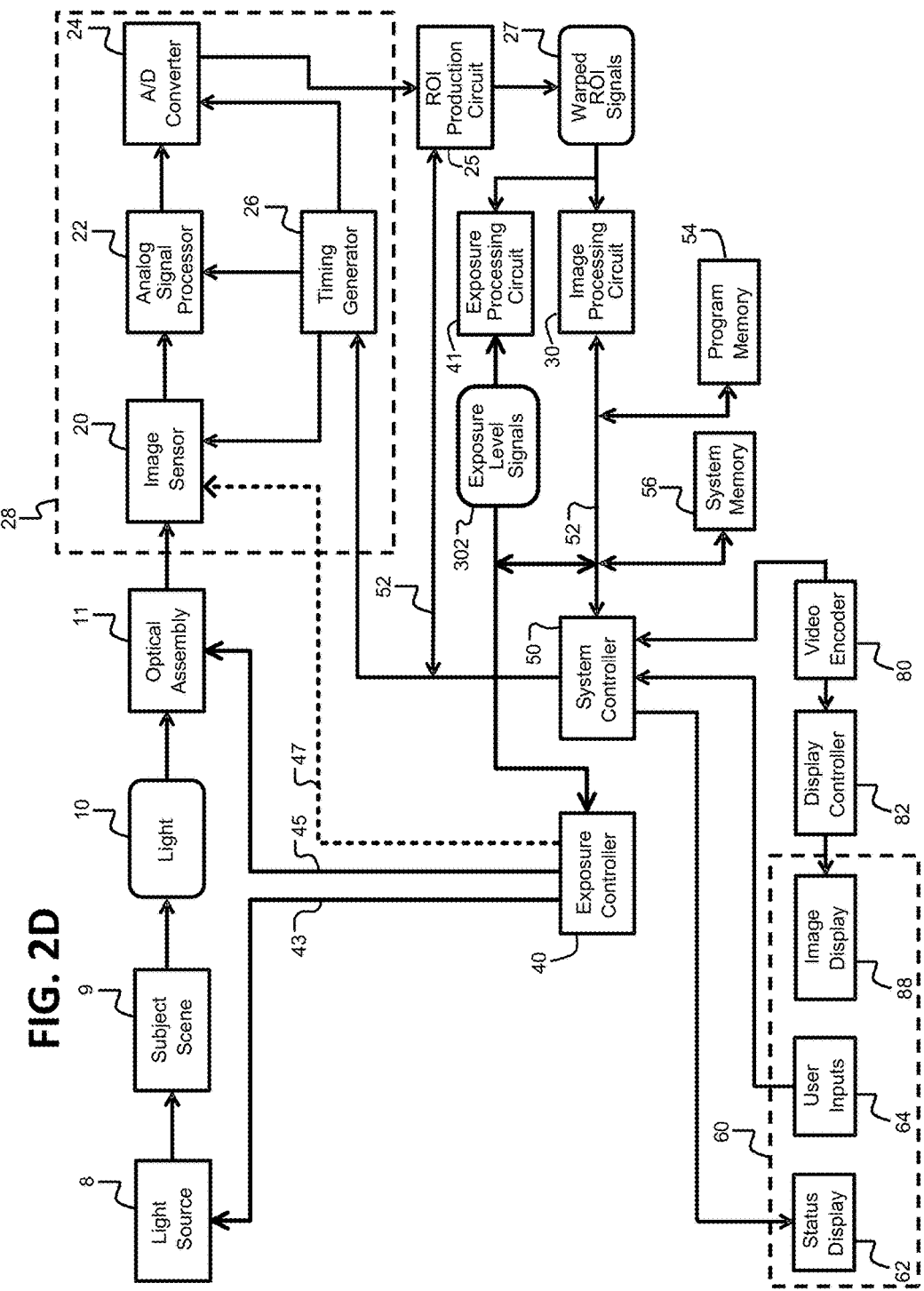
FIG. 2D is a hardware block diagram of another example image capture device with separate exposure processing circuitry.

FIG. 2D is a hardware block diagram of an image capture device according to another embodiment of the invention with a different hardware configuration. Generally, the depicted elements are similar to those of FIG. 2A, but the calculation of exposure level signals 302 is performed in exposure processing circuitry 41 separate from the image processing circuitry 30, such as in a separate signal processor or a digital logic device such as an FPGA. Exposure processing circuit 41 may also be integrated with exposure controller 40, for example in an FPGA or DSP. As shown, exposure processing circuitry 41 is separate from exposure controller 40 and connected to exposure controller 40 and system controller 50 via system bus 52. In this version, system controller 50 will typically send commands and model data to exposure processing circuit 41 to configure the circuit with an appropriate distortion model and resulting area stretch weights for the ROI currently selected by the user, as will be further discussed below with regard to the distortion models employed in some embodiments.

Importantly, in each of the example embodiments of the invention herein, the calculation of exposure level signals at depicted step 300 does not require the unwarped image signals 306 as its input. This allows an improved exposure control that accounts for the warping that might otherwise skew the exposure control process, yet still provides a fast enough signal that the exposure controller can perform real-time feedback control of the image capture device. Preferably, while data from the current image frame is being processed, the exposure feedback control signals are generated based on the current image frame are output to the imaging device. However, in some versions, the pixel counting process, and signal generation at the exposure controller 40, may cause delay in the control process that a delay of more than one frame is present before exposure feedback control signals 43, 45, and 47 are received at the imaging device. In such cases, the delay is still much shorter than that resulting from using the unwarped image data to perform exposure control, with resulting improvements in speed and stability of the exposure control.

Figure 3:
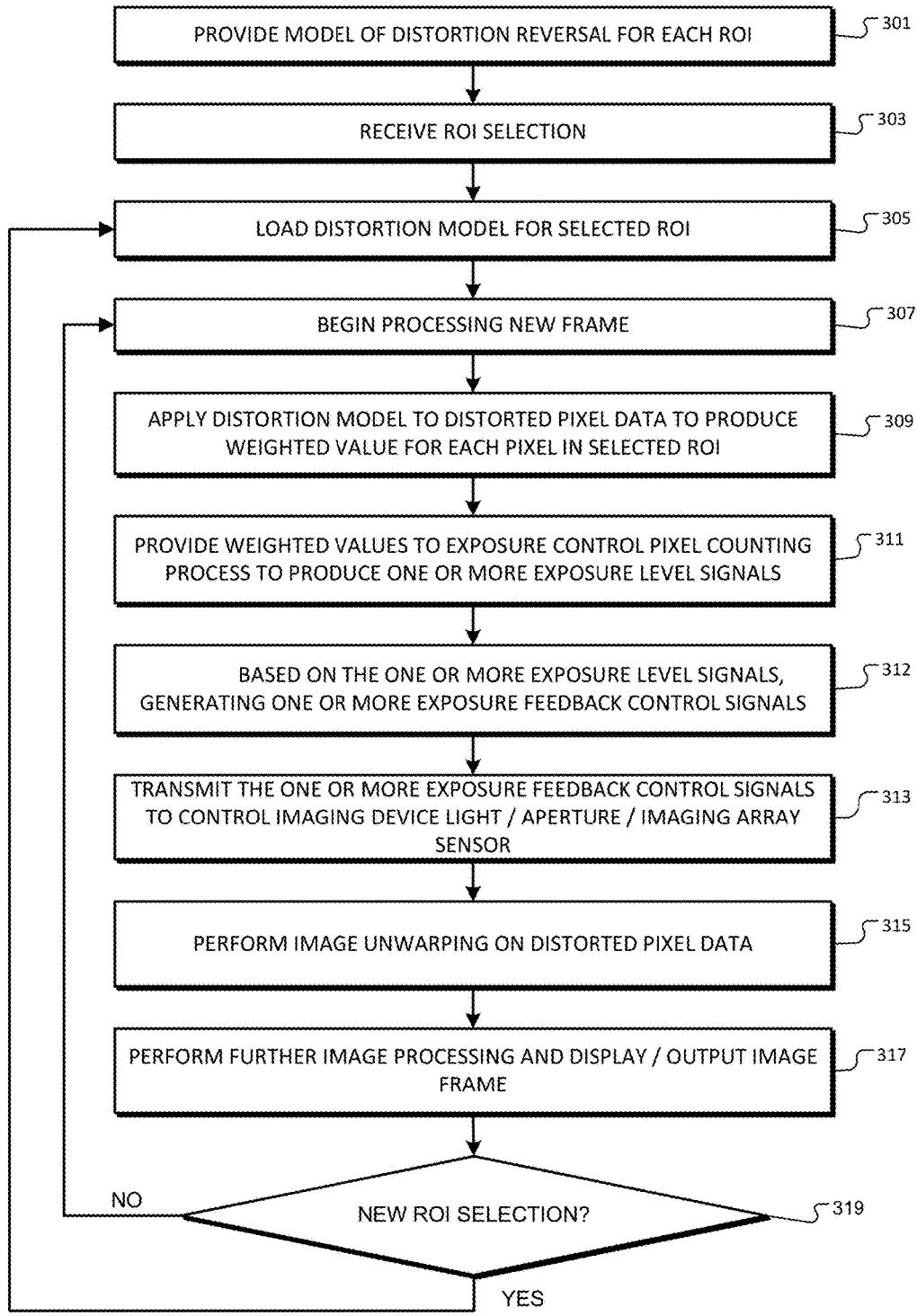
FIG. 3 is a flowchart of an exposure control process.

FIG. 3 is a flowchart of an exposure control process according to some embodiments, which may be employed with the example hardware and functional designs of FIGS. 2A-D, or may be employed with other hardware designated with a similar purpose. Generally the depicted process uses models of the distortion or warping produced by the wide angle lens in the imaging device, referred to as distortion models, which characterize the weight that each pixel in the ROI would have when producing an undistorted image, but without producing the image to calculate the weight. These models may be prepared in advance by the system designers, or may be calculated automatically through observation and characterization of the lens and optical system used, or the distortion present in the image data (such as the warped ROI signals 27) obtained from the device.

In any case, the depicted process begins at block 301 with providing a model of the distortion for each ROI for which the device may be configured to produce images. The process of constructing and providing such models is discussed further with respect to FIG. 4. When the invention is embodied in a solid-state look-around endoscope device, such as the device described in the incorporated U.S. Pat. No. 8,814,782, a distortion model is provided for each ROI which the device is capable of producing. In some versions, a device is capable of continuous movement within a range of movement, providing a large number of possible ROIs. In such case, while a model may be provided for each degree or fractional degree of movement, it is generally better to provide a model generator configured to automatically create the appropriate distortion models. Further, while the use of calculated distortion models to provide the desired pixel weights is preferred for speed of loading the models from system memory, other versions may store the distortion model as the raw pixel weights that characterize the distortion.

A new region of interest may be selected at step 303 or the process may begin with a default or last-used region of interest selection. Generally, the process of the user selecting a region of interest and the device producing the view of the selected region is described in U.S. Pat. No. 8,814,782, and will not be further described here to avoid repeating information unnecessarily. The process may include selecting from preset views, or receiving a panning command to move the view or otherwise choose a new angle at which the imaging device will operate and, in response, adjusting the image devices angle of operation and activating or loading from memory (block 305) a distortion model for performing exposure control at the new angle of operation. The exposure control process is typically implemented under control of software stored in system memory 56 and run on system controller 50 and image processing circuit 30. Some functions may be implemented in software or firmware of exposure controller 40 and exposure processing circuit 41. Note that the distortion models as referred to herein are separate and independent from the processes at block 315 used to unwarp the image data and produce unwarped image signals 32. At block 305, the image processing device and the exposure control circuitry start receiving a stream of distorted image frames produced at the newly selected ROI.

Next at block 307, the process begins processing a first frame or image from the stream of images. The processing of a frame is preferably completed before a new frame is received, allowing the depicted process loop to update the exposure control signals with each frame. The loop is preferably performed by exposure control program code and image processing program code executed on one or more devices as described above. The process at block 309, applies the distortion model to distorted pixel data to produce weighted pixel value for each pixel in selected ROI. This block, in the preferred version, multiplies the pixel intensity value, or other values controlling the lightness or perceived brightness of the pixel depending on what encoding the imaging processing system employs (such as the YCbCr and Y'CbCr color), for each pixel with the weight assigned to that pixel in the distortion model. That is, for each of a group of designated pixels defining a region of interest, the process scales a pixel intensity value by a respective pixel weight from the distortion model to produce a weighted pixel value for each respective pixel. It is noted that the pixels outside the ROI are not used. They may be zeroed out, or simply excluded from the calculation. Because the pixels actually used for the ROI vary for each ROI, some definition of the boundary of the pixels employed for each ROI is needed. The exclusion of pixels outside the ROI may be done before the application of the distortion model at block 309, or may be done concurrently. In some versions, the region of interest is circular, requiring an elliptical set of pixels from the distorted image data contained in warped ROI signals 27. Such an ellipse may be defined by its center and axes lengths, and then multiple ROI's of a particular device may be defined by coefficients describing a curve of the two axes lengths versus angle of view. In this manner, the ROI boundaries may be stored and retrieved without storing an entire mask or boundary coordinates for each ROI.

The process next goes to block 311 where the weighted pixel values are fed to a pixel counting process to produce one or more exposure level signals. Block 311 may be performed by dedicated circuitry such as exposure processing circuit 41 (FIG. 2D), or by the image processor 30 or the exposure controller 40 executing exposure control program code. A single exposure level 302 signal may be calculated by counting the pixels whose weighted pixel value is above a designated threshold. In some versions, multiple exposure level signals 302 may be calculated. For example, exposure level signals may be calculated indicating a spatial distribution of the brightness corresponding to the ROI, or exposure level signals may be calculated for sub-regions of the ROI. Further, exposure level signals may be calculated based on identifying one or more features in the ROI and calculating levels corresponding to the brightness of those features separate from the overall ROI exposure pixel counting. In such versions, the process may require dedicated hardware in the form of exposure processing circuit 41.

The process at block 312 then, based on the exposure level signals 302, generates one or more exposure feedback control signals. Block 312 is typically performed by exposure control program code running on exposure controller 40, but these functions may be integrated with other controller circuits such as system controller 50, for example. In the simplest forms, block signals to increase or decrease the brightness of the device light if the exposure level signal is under or over a desired threshold, or adjust the image sensor integration time accordingly. The aperture may also be adjusted. The exposure feedback control signals may also be based on other variables such as the distance to the subject scene. The feedback control signals may be generated entirely at exposure controller 40, or some of the calculations or comparisons needed to generate the exposure feedback control signals from the exposure level signals may be performed by the device that calculates the exposure level signals (exposure processing circuitry 41 or image processing circuit 30), and then transmitted to exposure controller 40.

Next, at block 313, the process transmits the one or more exposure feedback control signals to the imaging device in such a manner that they control exposure features of the imaging device for subsequent frames in the series of sequential image frames. These signals will typically include light source control signal 43, aperture control signal 45, and integration time control signal 47. Other signals may also be generated based on the exposure level signals to control other features on the imaging device.

Next at block 315, the process producing an undistorted version of the image frame, the unwarped ROI signals 306 (FIG. 2C) typically using known methods of linear interpolation based on the specific warping resulting from the system optics. This block is typically done in the image processor 30 by executing image processing program code. Next at block 317, further image processing steps may be performed as for display and output of the image having the desired view.

Figure 4:
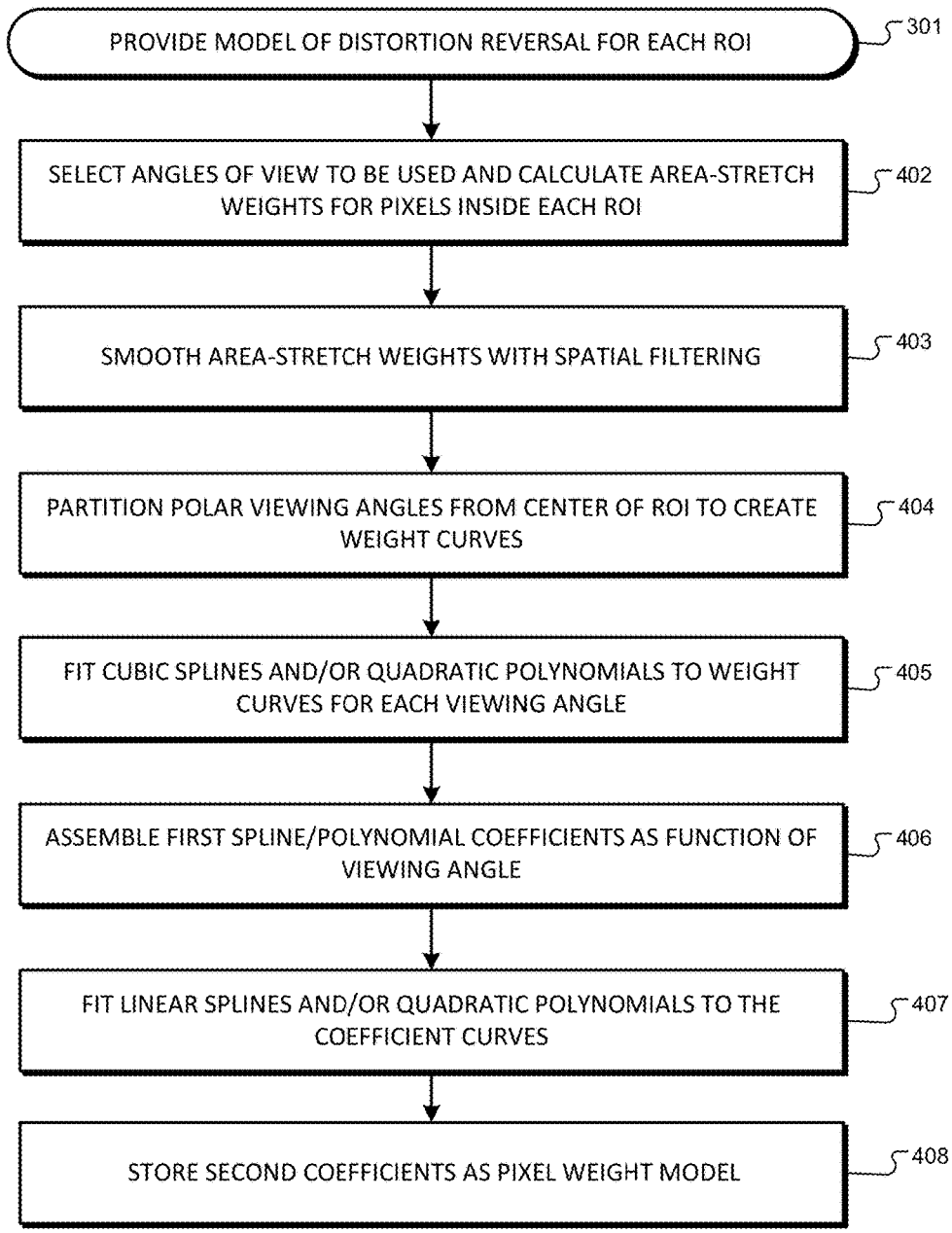
FIG. 4 is a flowchart for an example process of constructing and providing a distortion model.

FIG. 4 is a flowchart for an example process of constructing and providing a distortion model according to an example embodiment. Generally the models are created with the following considerations.

Area-Stretch Weighting

Since the pixels outside of the ROI are not used to form the displayed image, it is better to exclude them from the exposure control calculations. For the pixels inside the ROI, some of them will be used more frequently than others during the interpolation of the displayed image. This is because a small area in the sensor image may get unwarped into a relatively larger displayed image area than another small area on the sensor image. Therefore, the distortion models a weight for each pixel accounting for ROI pixels that get "stretched out" more than others that get "stretched out" less. An example group of area stretch weights for an example ROI is shown in the 3D graph of FIG. 6, which shows the vertical axis as the area stretch weight value for a pixel, and the two horizontal axes as the X-Y locations of pixels. As can be seen in the graph, the elliptical ROI depicted is toward one end of the range of movement of the device, with the left-side depicted edge pixels given more weight in the exposure control because they contribute to more pixels in the undistorted image.

Exposure Control Area-Stretch Weight Model

Bilinear interpolation of the sensor image can be used to produce the unwarped displayed image data based on the known distortion from the system optics. Other image interpolation method can also be used. If, for all sensor pixels in the ROI, every time a sensor pixel is used in the interpolation, the pixel's interpolation weight is accumulated, the interpolation process provides a measure of how much area each sensor pixel covers in the display image, quantified as an area-stretch weight. This procedure will generate a 2-dimensional surface in a 3-dimensional space with x-coordinate, y-coordinate, and area-stretch weight as the three axes. For a given set of optics (i.e. FOV, actual viewing angle, and distortion characteristic function), one such 2-D surface can be created for each angle of view (see FIG. 6). Given that it may be desired to have many available viewing angles (e.g. 0 degrees to 60 degrees in steps of 0.1 degree), it is generally much less burdensome to use area-stretch weights only if there is a simple model to generate them (the alternative is to store an entire frame's worth of weights for each available angle of view). Fortunately, the radial distortion symmetry of the optics allows for creation of a suitable distortion models.

Referring to the flowchart of FIG. 4, an example process is given to provide distortion models (block 301) for each ROI provided by the device. To create the distortion models, a number N angles of view are selected (e.g. 0 degrees to 30 degrees in steps of 1 degree) and the corresponding area-stretch weights are calculated at block 402, resulting in weights for each pixel, which may be considered as a surface for each ROI when graphed with pixel x-y locations as in the example weight surface of FIG. 6. The area-stretch weight surfaces can have fine structures, depending on how the sensor pixel lattice lines up with the new pixel lattice within a small area of the new, unwarped, image. It can therefore be understood after appreciating this disclosure that there are many possible ways to create distortion models, some of which may be better for differing types of optics and image sensor combinations. The process described here is only one example which provided good results for an SSLA endoscope embodiment as described herein.

To produce a simple model from the weight surfaces, the process at block 403 first smoothes the area-stretch weights by filtering, in this case using a minimum filter with a 7×7 window followed by an 11×11 boxcar filter. For area-stretch weight surfaces that do not exhibit fine structures on the weight surfaces, such filtering may not be required.

Next the process at block 404 partitions the data for each surface according to the polar angle phi, into 288 bins. This number will, of course, tend to vary and may be higher as higher resolution devices are created giving many more pixels in each bin at the outer edge of the surface. To find phi at each pixel location, the process uses phi=a tan 2(x−X/2, y−Y/2). That is, the process shifts the coordinate system from the upper left to the center of the ROI. Bin the weights into the appropriate phi bin, keeping track of the associated radii. To find the radius r at each pixel location, use r=sqrt((x−X/2)^2+(y−Y/2)^2). There should be now (288 bins/angle of view)*(N angles of view) weight curves as functions of radius.

Figure 7B:
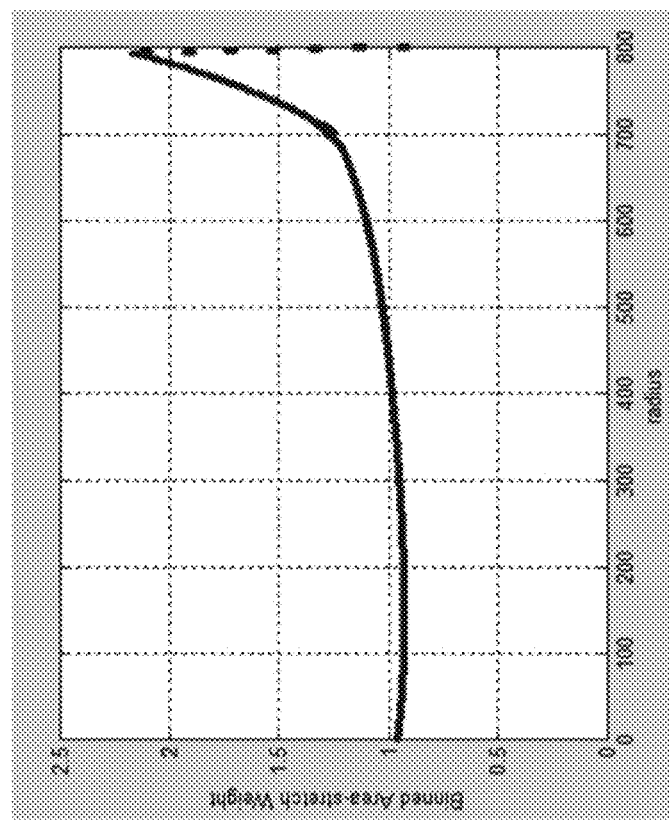
FIGS. 7A-B show two example curves of binned area-stretch weights.
Figure 7A:
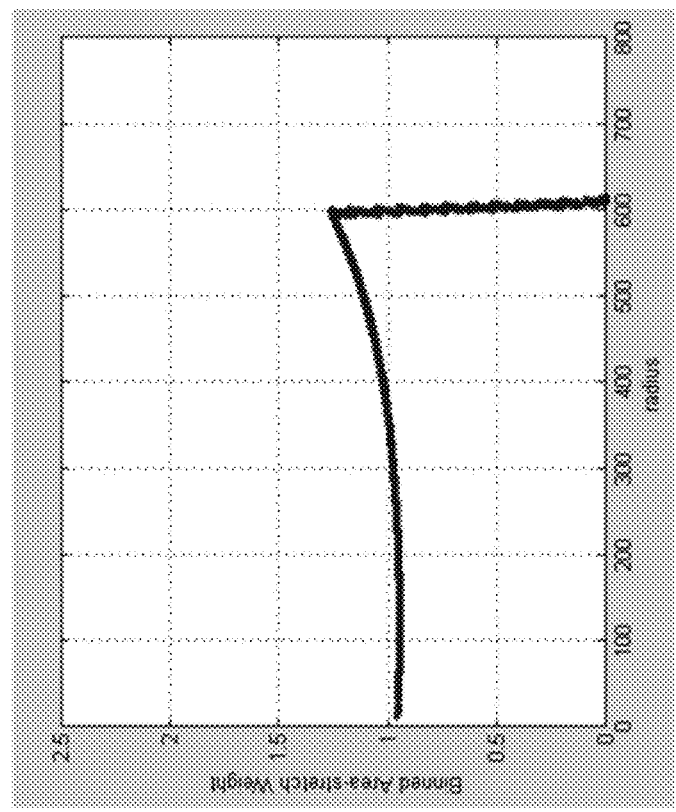

Using the weight curves, the process at block 405 now finds coefficients to describe the weight curve. In this version, the process fits a series of cubic splines or quadratic polynomials to the weight curve for each viewing angle. Of course, other suitable functions may be used to produce coefficients describing the weight curves. The selection of how many splines, polynomials, or other functions to use will vary depending on device. For this version, the curves fitting is done as follows:

For each angle of view, the process picks the phi bin that has the largest domain in r. FIGS. 7A-B show two example curves of binned area-stretch weights. The bin on the right has a larger domain than the bin on the left, but there is good agreement between them for the common-domain portion. Each bin has some common domain with this largest-domain bin, and they have good agreement in the common domain. Next the process finds the knee of each weight curve, which is the radius value where the slope suddenly increases (the data tends to "bunch up" there). This can be done by taking the derivative of the curve and checking for a maximum above a specified value, for example. On the curve of FIG. 7B the knee can be seen to be about r=700. If there is no knee, the process finds the endpoint of the good data. On the curve of FIG. 7A, there is no knee and the endpoint of the good data is about 600 (the sharp drop-off that starts around 600 is just an edge artifact due to the edge of the interpolation area).

Next, the curves are to create a first set of coefficients, which may be referred to as distortion curve coefficients, using these steps: Fit a cubic spline (rCi) with three knots to each weight curve below the curve knee (or endpoint if there is no knee). The first knot should be at zero radius, the third knot will either be at the knee if it exists or at the endpoint. Fit a quadratic polynomial (rQi) to the data above the knee. Constrain the quadratic to have a value equal to the cubic spline fit at the knee. If there is no knee, there is no need to fit the quadratic polynomial. This is done because a good fit cannot be obtained with a single spline without significantly increasing the number of knots or increasing the order of the spline or both. By splitting the data into two segments, below and above the knee, two good and simple fits can be obtained. A potential drawback of fitting in this way is that the gradient is not guaranteed to be smooth across the knee point. This is not expected to cause any problems because the fitted result is not applied to a displayed image (in which case gradient jumps cause visual artifacts). While splines and quadratic polynomials are used in this version, other functions may be to fit the curves.

Beginning at block 406, the process uses the results of the curve splitting to create a model of the curves that can be applied across different viewing angles. Now there should be (4 parameters per cubic spline segment)*(2 cubic spline segments)+(3 parameters per quadratic segment)*(1 quadratic segment) different parameters, each with N values. These parameters (both coefficients and knot and knee values) are arranged as functions of the N angles of view at block 406. If the knees and the endpoints are well-chosen, the resulting curves should be relatively well-behaved. Block 406 also assembles all the spline knots as functions of viewing angle, and assembles all the knee values as a function of viewing angle.

The process then takes these functions, and at block 407 fits curves to these coefficient values to model functions them as a function of viewing angle. In this version, this block involves fitting a quadratic polynomial (aQci) to each of the cubic spline coefficients. It also fits a quadratic polynomial to each of the quadratic polynomial coefficients (aQqi). It fits a linear spline with three knots to the two non-zero rCi spline knots (linear splines aL1ci and aL2ci). It fits a linear spline with three knots (aLk) to the knee data. All of these will be functions of viewing angle. The resulting second set of coefficients make up the models that can be stored and later evaluated to provide a distortion model for each angle of view. At block 408, the coefficients for aQci, aQqi, aL1ci, aL2ci, and aLk are stored in memory for later retrieval by the system to conduct exposure control.

Exposure Control Area-Stretch Weight Model Implementation

Figure 5:
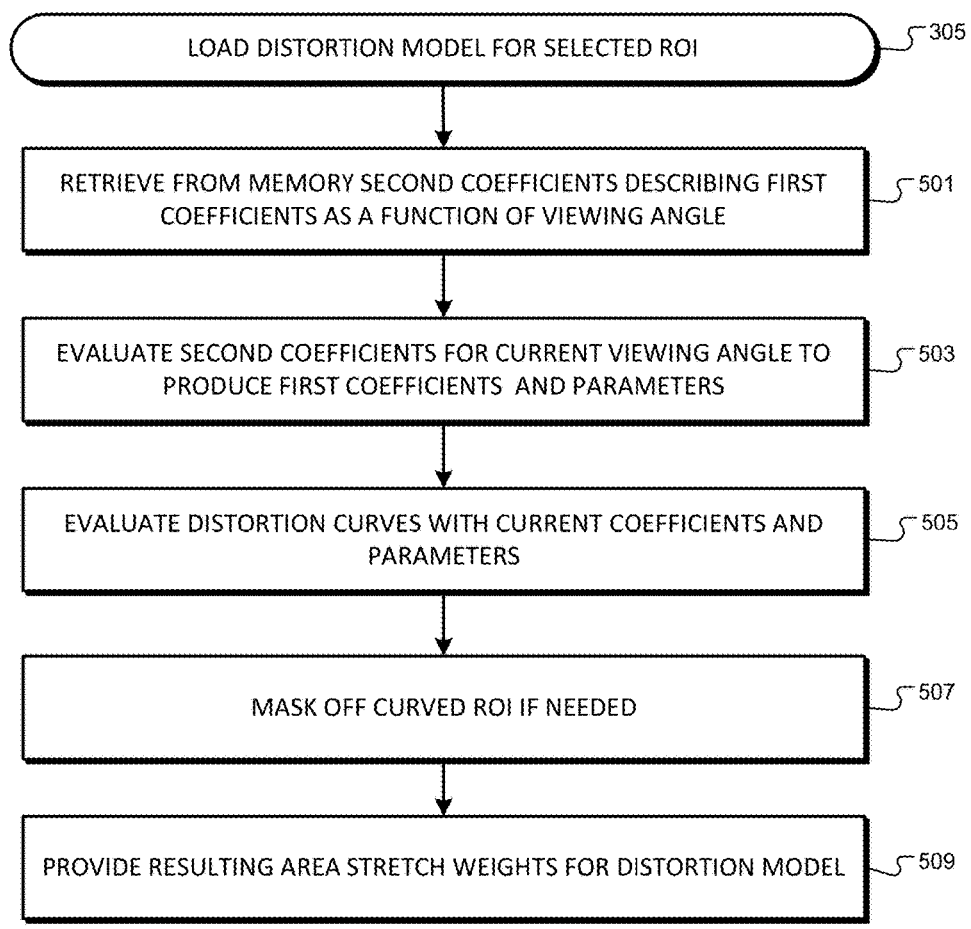
FIG. 5 is a flowchart of a process for loading and activating a distortion model for a selected ROI.

FIG. 5 is a flowchart of a process for loading and activating a distortion model for a selected ROI, which may use a model produced according to the process of FIG. 4 or another suitable model. The process of loading and activating a distortion model for the selected ROI may be conducted once for every image frame processed, in versions where an FPGA or other dedicated digital logic arrangement is used, or may be done each time the ROI is changed, as shown in the process of FIG. 3. The process generally implements block 305 of loading a distortion model for a selected ROI. At block 501, the process retrieves the second coefficients from memory, which describe curves the first coefficients as a function of viewing angle or viewing position of the device. For models produced as described above, this includes retrieving the coefficients for the two quadratic splines aQci and aQqi from memory, and retrieving the coefficients for the linear splines aL1ci, aL2ci, and aLk from memory, that is the curves that describe the knot and knee values as well.

Next at block 503, the process evaluates the second coefficients to produce the desired first coefficients at the current viewing angle, that is, the angle or position of the desired ROI. For the model above, this block includes evaluating splines as functions of the current viewing angle. The set of results defines the spline rCi and the polynomial rQi that are needed for the current ROI or image frame. Next at block 505, the resulting curves are then evaluated at each pixel location in the desired ROI to provide the modeled area-stretch weight. In the example model above, this block includes evaluating the spline rCi or the polynomial rQi as a function of the radius. This is done once for each pixel location in the image. The result at each pixel location is the area-stretch weight for that pixel location.

Next at block 507, the process may apply a mask to mask-off or set to zero those weights which are not used in the current ROI. This is preferably done by multiplying area stretch weights by zero if they are outside the ROI, and by 1 if they are inside. This step sets to zero the weight for pixels outside of the ROI, and is typically used for a curved or circular ROI. The resulting set of weights is provided as the distortion model (block 309 of FIG. 3) for the exposure control process.

As used herein the terms "comprising," "including," "carrying," "having" "containing," "involving," and the like are to be understood to be open-ended, that is, to mean including but not limited to. Any use of ordinal terms such as "first," "second," "third," etc., in the claims to modify a claim element does not by itself connote any priority, precedence, or order of one claim element over another, or the temporal order in which acts of a method are performed. Rather, unless specifically stated otherwise, such ordinal terms are used merely as labels to distinguish one claim element having a certain name from another element having a same name (but for use of the ordinal term).

The foregoing has outlined rather broadly the features and technical advantages of the invention in order that the detailed description of the invention that follows may be better understood. It should be appreciated by those skilled in the art that the conception and specific embodiments disclosed may be readily utilized as a basis for modifying or designing other structures for carrying out the same purposes of the invention. It should also be realized by those skilled in the art that such equivalent constructions do not depart from the scope of the invention as set forth in the appended claims.

Although the invention and its advantages have been described in detail, it should be understood that various changes, substitutions and alterations can be made herein without departing from the spirit and scope of the invention as defined by the appended claims. The combinations of features described herein should not be interpreted to be limiting, and the features herein may be used in any working combination or sub-combination according to the invention. This description should therefore be interpreted as providing written support, under U.S. patent law and any relevant foreign patent laws, for any working combination or some sub-combination of the features herein.

Moreover, the scope of the present application is not intended to be limited to the particular embodiments of the process, machine, manufacture, composition of matter, means, methods and steps described in the specification. As one of ordinary skill in the art will readily appreciate from the disclosure of the invention, processes, machines, manufacture, compositions of matter, means, methods, or steps, presently existing or later to be developed that perform substantially the same function or achieve substantially the same result as the corresponding embodiments described herein may be utilized according to the invention. Accordingly, the appended claims are intended to include within their scope such processes, machines, manufacture, compositions of matter, means, methods, or steps.

The invention claimed is:

1. An imaging scope system, comprising:
a light emitting element;
an optical assembly including a wide angle lens element;
an image sensor assembly including an image sensor configured to receive at least a portion of light focused through the optical assembly and produce output signals;
image forming circuitry adapted to receive the output signal and produce an image signal including distortion resulting from the wide angle lens element;
exposure control circuitry coupled to receive the image signal from the image forming circuitry, and controllably coupled to at least one of the light emitting element, the image sensor, and the optical assembly, and further configured to:
(a) model an inverse effect of the distortion by (i) estimating pixel weights that respective pixels of the image signal including distortion have when producing an undistorted version of the image signal; (ii) scaling pixel intensity values by respective pixel weights to produce a weighted pixel value for the respective pixels;
(b) provide the weighted pixel values to an exposure control pixel counting process to produce one or more exposure feedback control signals; and
(c) transmit the one or more exposure feedback control signals to at least one of the light emitting element, the optical assembly, and the image sensor assembly; and
image processing circuitry configured to receive the image signal including distortion and produce an undistorted version of the image signal.

2. The system of claim 1 in which the exposure control circuitry is configured to operate in parallel to the image processing circuitry.

3. The system of claim 1 in which the exposure control circuitry is configured to provide the weighted pixel values to the exposure control pixel counting process as part of a digital signal processing sequence before the image processing circuitry produces the undistorted version of the image signal.

4. The system of claim 1 in which the image forming circuitry further includes image selecting circuitry that receives the image signal and produces a region of interest signal that corresponds to a region of interest that is less than the image.

5. The system of claim 1 in which the exposure control circuitry is formed in a field programmable gate array (FPGA).

6. The system of claim 1 in which the exposure control circuitry comprises a graphics processing unit (GPU).

7. The system of claim 1 in which estimating pixel weights further includes evaluating first coefficients which describe curves from which the weight of a respective pixel is calculated using the respective pixel's coordinates.

8. The system of claim 7, in which the first coefficients include cubic spline coefficients and quadratic polynomial coefficients.

9. The system of claim 7, in which the first coefficients are produced by evaluating second coefficients of second curves which describe the values of the first coefficients as a function of a viewing angle of the device.

10. A method of controlling an imaging device, comprising:
(a) receiving a series of sequential image frames including multiple pixels from an imaging device having a wide angle lens producing distortion in the image frames;
(b) activating a first distortion model for estimating a pixel weight that respective designated pixels have in an undistorted version of an image frame;
(c) performing exposure control of the imaging device by:
for each of a group of designated pixels defining a region of interest, scaling a pixel value by a respective pixel weight from the first distortion model to produce a weighted pixel value for each respective pixel;
providing the weighted pixel values to an exposure control pixel counting process to produce one or more exposure level signals;
based on the one or more exposure level signals, generating one or more exposure feedback control signals;
transmitting the one or more exposure feedback control signals to the imaging device in such a manner that they control exposure features of the imaging device;
(d) producing an undistorted version of the image frame.

11. The method of claim 10 further comprising receiving a new angle at which the imaging device will operate and, in response, adjusting the image devices angle of operation and activating a second distortion model for performing exposure control at the new angle of operation, and receiving a stream of image frames produced at the new angle.

12. The method of claim 10 in which at least one of the one to more exposure feedback control signals controls the integration time on an imaging array sensor of the imaging device.

13. The method of claim 10 in which one of the one or more exposure feedback control signals controls the brightness of a light source of the imaging device.

14. The method of claim 10 in which one of the one or more exposure feedback control signals controls the aperture of the imaging device.

15. The method of claim 10, where in activating a distortion model includes evaluating first coefficients which describe curves from which the weight of a respective pixel is calculated using the respective pixel's coordinates.

16. The method of claim 15, in which the first coefficients include cubic spline coefficients and quadratic polynomial coefficients.

17. The method of claim 10, in which the performing exposure control of the imaging device is done independently of producing the undistorted versions of the image frames.

18. The method of claim 10, in which the imaging device is a medical scope configured to allow a user to select from multiple regions of interest viewing at multiple respective angles of view, the method further comprising storing a respective distortion model for each of the regions of interest.

19. Exposure control circuitry operable to receive an image signal that includes distortion resulting from a wide angle lens element and operable to control at least one of a light emitting element, an image sensor, and an optical assembly including the wide angle lens, the exposure control circuitry further configured to:
  (a) model an inverse effect of the distortion by (i) estimating pixel weights that respective pixels of the image signal including distortion have when producing an undistorted version of the image signal; (ii) scaling pixel intensity values by respective pixel weights to produce a weighted pixel value for the respective pixels;
  (b) provide the weighted pixel values to an exposure control pixel counting process to produce one or more exposure feedback control signals; and
  (c) transmit the one or more exposure feedback control signals to at least one of the light emitting element, the optical assembly, and the image sensor assembly.

20. The circuitry of claim 19 in which the exposure control circuitry is further configured to receive a new angle at which the imaging device will operate and, in response, activate a second distortion model for performing exposure control at the new angle of operation, and receive a stream of image frames produced at the new angle.

* * * * *